United States Patent
Chen et al.

(10) Patent No.: US 11,633,222 B2
(45) Date of Patent: Apr. 25, 2023

(54) BONE CEMENT MIXING ASSEMBLY

(71) Applicant: XELITE BIOMED LTD., New Taipei (TW)

(72) Inventors: Hsiu-Chuan Chen, New Taipei (TW); Chung-Wei Kao, New Taipei (TW); Yung-He Liang, New Taipei (TW); Chih-Tai Yu, New Taipei (TW)

(73) Assignee: XELITE BIOMED LTD., New Taipei (TW)

( * ) Notice: Subject to any disclaimer, the term of this patent is extended or adjusted under 35 U.S.C. 154(b) by 0 days.

(21) Appl. No.: 17/541,983

(22) Filed: Dec. 3, 2021

(65) Prior Publication Data
US 2022/0175435 A1    Jun. 9, 2022

(30) Foreign Application Priority Data
Dec. 4, 2020  (TW) ................................ 109142721

(51) Int. Cl.
| | | |
|---|---|---|
| *A61B 17/88* | (2006.01) |
| *B01F 35/32* | (2022.01) |
| *B01F 33/501* | (2022.01) |
| *B01F 23/53* | (2022.01) |
| B01F 101/20 | (2022.01) |
| A61B 17/00 | (2006.01) |

(52) U.S. Cl.
CPC .......... *A61B 17/8833* (2013.01); *B01F 23/53* (2022.01); *B01F 33/50112* (2022.01); *B01F 35/3202* (2022.01); *A61B 2017/00477* (2013.01); *A61B 2017/00902* (2013.01); *A61B 2017/8838* (2013.01); *B01F 2101/20* (2022.01)

(58) Field of Classification Search
CPC ... A61B 17/88; A61B 17/8833; B01F 33/501; B01F 33/50112; B01F 23/53; B01F 35/3202
See application file for complete search history.

(56) References Cited

U.S. PATENT DOCUMENTS

| | | | |
|---|---|---|---|
| 8,833,606 B2 * | 9/2014 | Graham | B01F 27/0721 206/229 |
| 9,616,454 B2 * | 4/2017 | Staub | A61C 5/64 |
| 10,596,069 B2 * | 3/2020 | Goodman | A61M 5/3145 |

FOREIGN PATENT DOCUMENTS

| | | |
|---|---|---|
| CN | 203829028 U | 9/2014 |
| CN | 105147384 B | 6/2017 |
| CN | 110801276 A | 2/2020 |

\* cited by examiner

*Primary Examiner* — Christopher J Beccia
(74) *Attorney, Agent, or Firm* — Muncy Geissler Olds & Lowe P.C.

(57) ABSTRACT

The invention provides a bone cement mixing assembly including a mixer, a syringe barrel and a movable plug cover. The mixer includes a stirring rod and a stirring barrel. The stirring rod has holding end, a rod body and a stirring end. The stirring barrel has a barrel cover, a first barrel open, a first barrel body, a first barrel bottom, and a stirring space located in the first barrel body. The syringe barrel has a second barrel open, a second barrel body, a second barrel bottom, and an injection space located in the second barrel body. In this way, the complete-stirred bone cement in the stirring barrel can be directly collected and pushed into the syringe barrel through the movement of the movable plug cover to achieve the effect of completing the preparation of the bone cement quickly and efficiently.

12 Claims, 12 Drawing Sheets

BONE CEMENT MIXING ASSEMBLY

BACKGROUND OF THE INVENTION

1. Field of the Invention

The present invention relates to a mixing equipment for medical use, in particular to a bone cement mixing assembly

2. Description of the Related Art

Bone cement is a kind of medical material for orthopedic filling use with polymethylmethacrylate (PMMA) as the main ingredient. It is mostly used to fill cavities form tooth decay, artificial joint replacement surgery, cementation vertebroplasty surgery and other orthopedic surgery for filling or bonding purposes.

Traditional bone cement has low viscosity and high fluidity. Therefore, if the injected amount is not appropriate during the operation, it is easy to cause the bone cement to leak out from the cracks of the bone, and then damage the surrounding nerves, muscles or cartilage tissues, which causes patient's discomfort and sequelae after the surgery. In order to solve such problems, many manufacturers have recently developed new bone cements. These new bone cements have high viscosity and low fluidity, which reduces the leakage problem during the operation, thus greatly improving the safety of the operation, but the price is much more expensive.

During the material preparation process before surgery, the powder and liquid must be thoroughly mixed and stirred. However, the mixing process of high-viscosity bone cement is not only quite laborious, but also agglomerates this high-viscosity bone cement into many clumps of different sizes after mixing, which need to be collected one by one and transferred into a syringe before surgery use. If the recovery rate of the mixed bone cement is too low, it will undoubtedly cause unnecessary waste. But it will take too much time if the mixed bone cement is collected carefully, which will likely cause the bone cement to solidify and become unusable during the collection period.

Therefore, how to quickly and efficiently prepare this high-viscosity bone cement is an urgent problem to be solved in practice.

SUMMARY OF THE INVENTION

The present invention has been accomplished under the circumstances in view. It is the main object of the present invention to provide a bone cement mixing assembly, which can quickly and efficiently complete the preparation of bone cement.

In order to achieve the foregoing object, the present invention provides a bone cement mixing assembly, which comprises a mixer, a syringe barrel, and a movable plug cover. The mixer comprises a stirring rod and a stirring barrel. The stirring rod comprises a holding end, a rod body and a stirring end. The stirring barrel comprises a barrel cover, a first barrel open, a first barrel body, a first barrel bottom, and a stirring space. The stirring end movably passes through the barrel cover. The stirring space is located in the first barrel body. The first barrel bottom comprises an opening. The syringe barrel comprises a second barrel open, a second barrel body, a second barrel bottom, and an injection space located in the second barrel body. The second barrel bottom comprises an injection port. The movable plug cover has an outer diameter slightly less than or equal to the inner diameter of the stirring barrel and the inner diameter of the syringe barrel. The movable plug cover is movably arranged in the stirring space or the injection space. The first barrel open is optionally sleeved by the barrel cover or connected to the second barrel open. When the barrel cover is sleeved on the first barrel open, the stirring end movably passes through the barrel cover and extends into the stirring space. When the first barrel open is connected to the second barrel open, the stirring space and the injection space are connected to each other.

Through the above-mentioned component configuration and structural design, the bone cement mixing assembly provided by the present invention can directly collect and push the bone cement completed in the stirring barrel into the syringe barrel through the movement of the movable plug cover. When used for stirring high-viscosity bone cement, it can not only effectively improve the recovery rate of high-viscosity bone cement during the transfer process, but also the steps are simple, which can effectively reduce the time of the transfer process and achieve rapid and efficient completion of bone cement preparation.

DETAILED DESCRIPTION OF THE INVENTION

Please refer to FIGS. 1-6, the bone cement mixing assembly 10 provided by an embodiment of the present invention comprises a mixer 20, a syringe barrel 30 and a movable plug cover 40.

Figure 1:
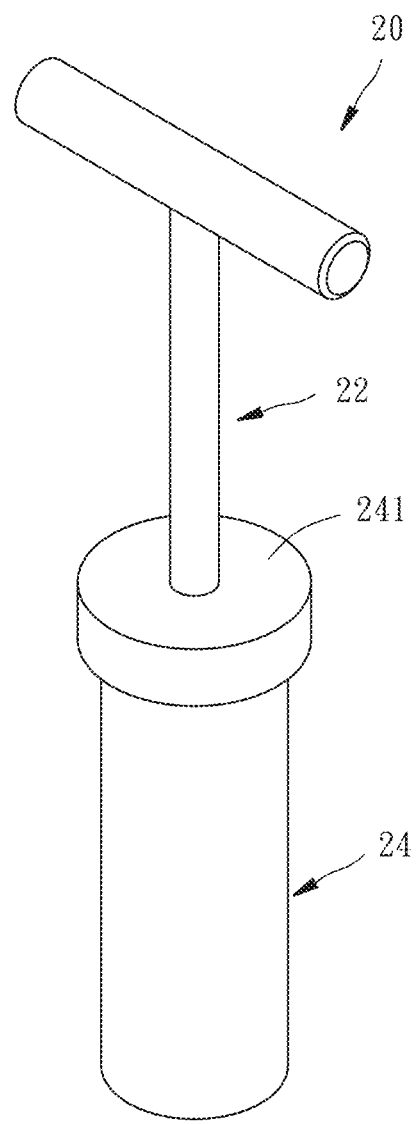
FIG. 1 is a partial assembly diagram of the bone cement mixing assembly provided by an embodiment of the present invention, which mainly shows the appearance of the mixer and the movable plug cover in the mixer when the bone cement is stirred.
Figure 3:
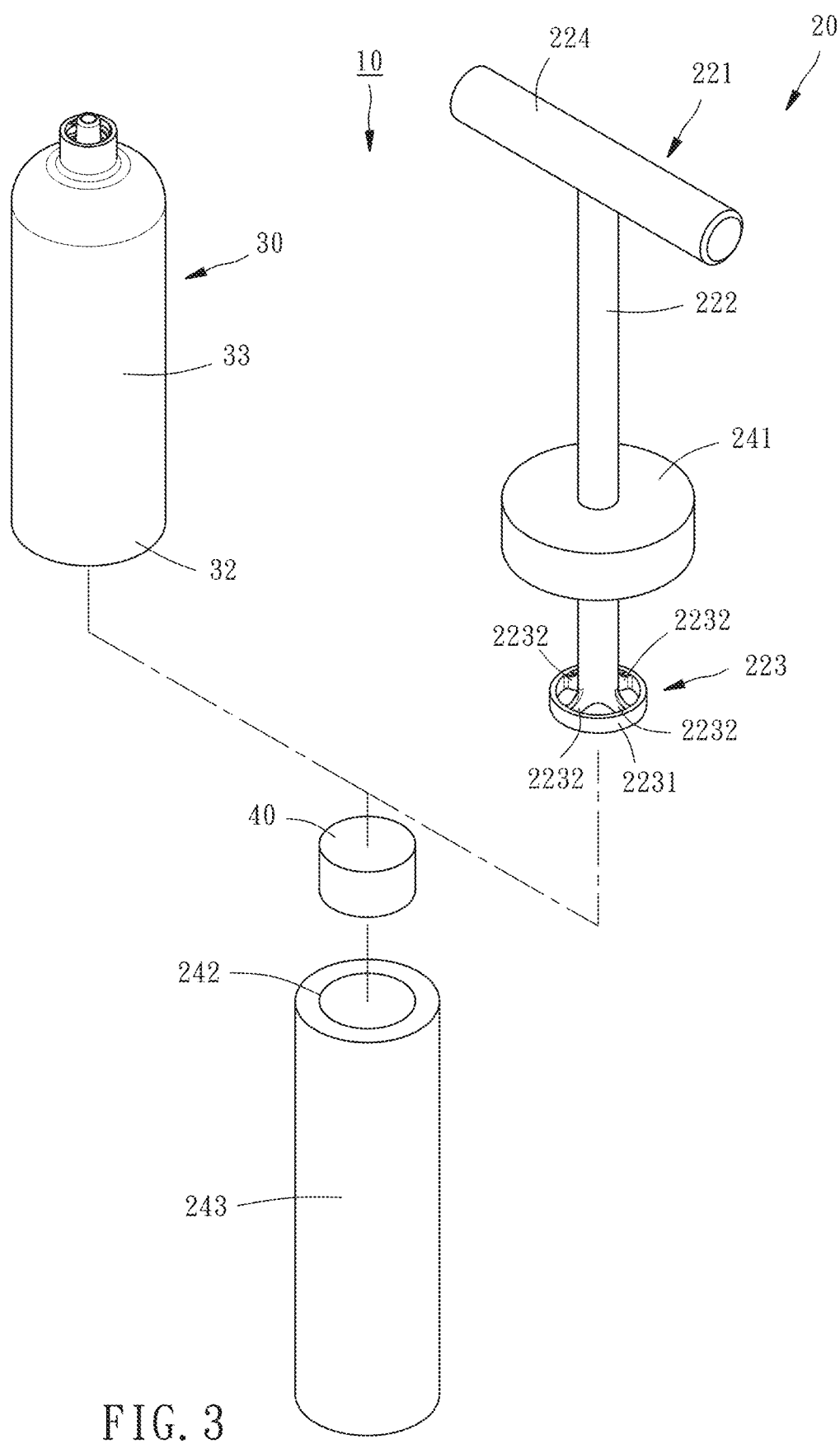
FIG. 3 is an exploded view of the bone cement mixing assembly provided by an embodiment of the present invention.
Figure 4:
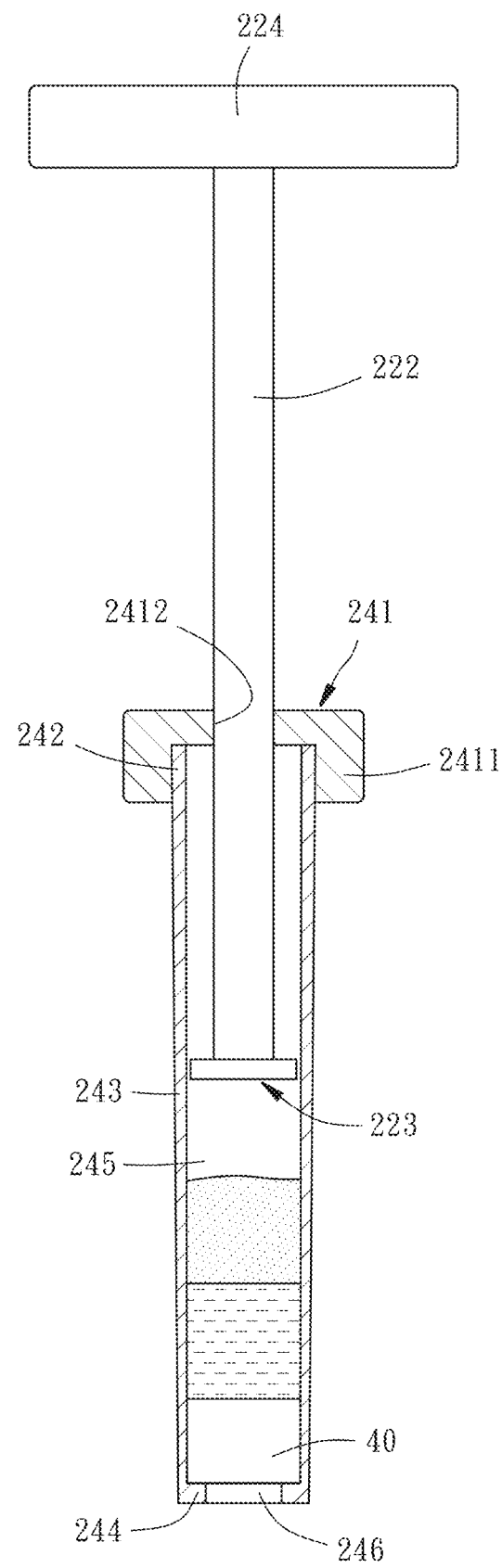
FIG. 4 is a cross-sectional view of FIG. 1, and shows the mixing of bone cement powder and liquid in the mixer.

As shown in FIGS. 1, 3 and 4, the mixer 20 comprises a stirring rod 22 and a stirring barrel 24. The stirring rod 22 has a holding end 221, a rod body 222 and a stirring end 223. The stirring barrel 24 has a barrel cover 241, a first barrel open 242, a first barrel body 243, a first barrel bottom 244 and a stirring space 245. The barrel cover 241 is detachably sleeved on the first barrel open 242. The stirring end 223 movably passes through the barrel cover 241. The stirring space 245 is located in the first barrel body 243. The first barrel bottom 244 has a opening 246.

In this embodiment, as shown in FIGS. 3 and 4, the holding end 221 further having a grip 224, and the grip 224 and the rod body 222 which forms a T-shape for grasping to mix the bone cement by the user. Moreover, the first barrel body 243 is made of transparent material, so that the user can observe the condition during stirring of the bone cement. Furthermore, as shown in FIG. 3, the barrel cover 241 is provided with a through hole 2412, and the rod body 222 is movably arranged in the through hole 2412. Finally, in this implementation, the stirring end 223 has a stirring ring 2231 and four connecting ribs 2232. One end of each connecting rib 2232 is connected to the rod body 222, and the other end of each connecting rib 2232 is connected to the stirring ring 2231. Such a ring structure is used to improve the mixing and stirring efficiency of bone cement.

Figure 2:
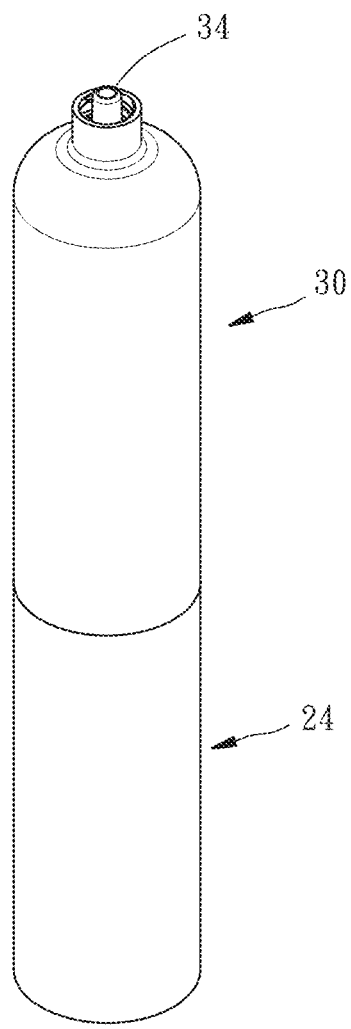
FIG. 2 is another partial assembly diagram of the bone cement mixing assembly provided by an embodiment of the present invention, which mainly shows the appearance of the combination of the mixer and the syringe barrel after the bone cement mixing is completed.
Figure 5:
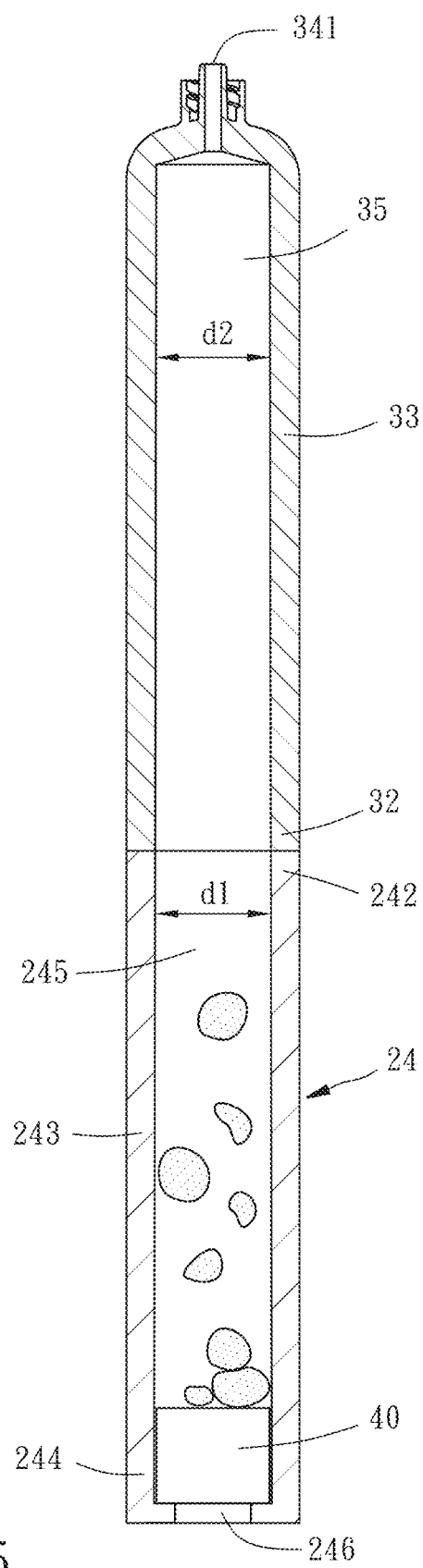
FIG. 5 is the cross-sectional view of FIG. 2, and shows that the complete-stirred bone cement in the mixer is ready for transfer.

As shown in FIGS. 2, 3 and 5, the syringe barrel 30 has a second barrel open 32, a second barrel body 33, a second barrel bottom 34, and an injection space 35 located in the second barrel body 33, and there is an injection port 341 at the second barrel bottom 34.

Figure 6:
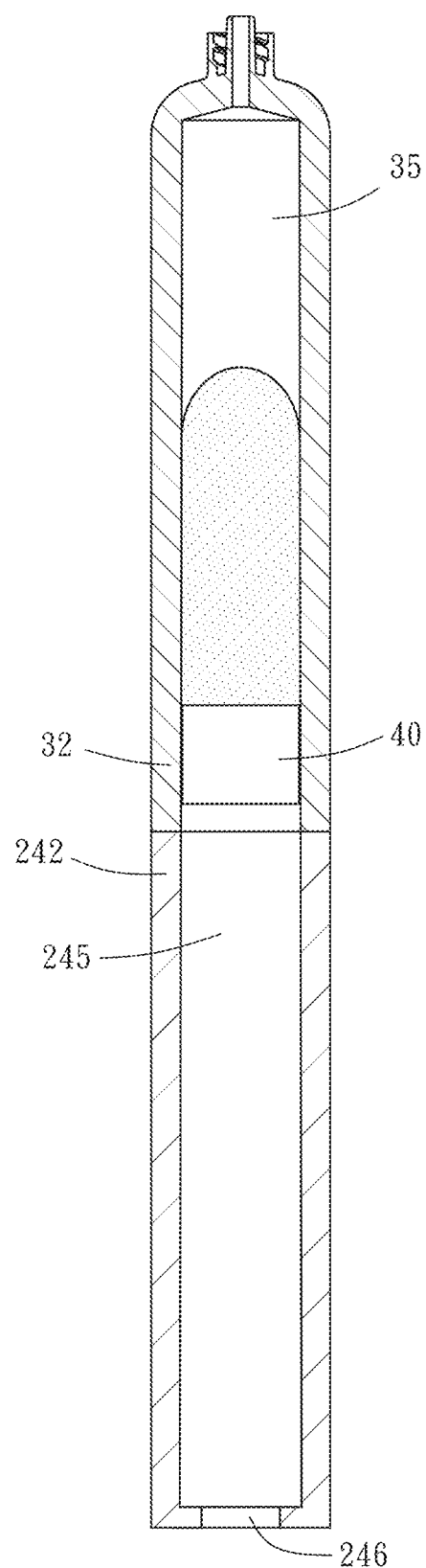
FIG. 6 is a cross-sectional view of FIG. 2, and shows the transfer of the complete-stirred bone cement to the syringe barrel.

The outer diameter D1 of the movable plug cover 40 is slightly smaller than or equal to the inner diameter d1 of the stirring barrel 24 and the inner diameter d2 of the syringe barrel 30, and is movably arranged in the stirring space 245 or the injection space 35, as shown in FIG. 5 and FIG. 6.

As shown in FIGS. 3 to 6, the first barrel open 242 can be optionally sleeved by the barrel cover 241 or connected to the second barrel open 32. When the barrel cover 241 is sleeved on the first barrel open 242, the stirring end 223 movably passes through the barrel cover 241 and extends into the stirring space 245 for stirring work. When the first barrel open 242 is connected to the second barrel open 32, the stirring space 245 and the injection space 35 are connected to each other. The inner diameter d1 of the stirring barrel 24 is equal to the inner diameter d2 of the syringe barrel 30.

The following describes how the user uses the bone cement mixing assembly 10 provided by the present invention to perform bone cement stirring work. As shown in FIGS. 3 to 6, first, the movable plug cover 40 is installed in the stirring barrel 24 near the first barrel bottom 244. At this time, the opening 246 of the first barrel bottom 244 will be covered by the movable plug cover 40, and the liquid and powder of the bone cement material can be poured into the stirring space 245 in sequence. After the barrel cover 241 is sleeved on and seals the first barrel open 242, the stirring end 223 can be used to mix and stir the bone cement. After the stirring is completed, the bone cement will agglomerate into many clumps of different sizes and adhere to the inner wall of the stirring barrel 24. At this time, the barrel cover 241 and the first barrel open 242 can be separated to take out the stirring rod 22.

Then, the first barrel open 242 is connected to the second barrel open 32. At this time, the stirring space 245 in the stirring barrel 24 will also communicate with the injection space 35 in the syringe barrel 30, so that the stirring space 245 and the injection space 35 together form a bone cement transfer channel. Since the inner diameters of the stirring space 245 and the injection space 35 are the same, as long as a push rod (not shown) pushes the movable plug cover 40 from the opening 246 of the first barrel bottom 244, the movable plug cover 40 and all the bone cement adhered to the inner wall of the stirring barrel 24 can be collected and pushed from the stirring space 245 to the injection space 35. When all the complete-stirred bone cement is pushed into the syringe barrel 30, the stirring barrel 24 can be removed, and the syringe barrel 30 loaded with bone cement can be installed with a plunger and an injection needle for clinical operation.

Through the above-mentioned component configuration and structural design, the bone cement mixing assembly 10 provided by the present invention can directly collect and push the complete-stirred bone cement from the stirring barrel 24 into the syringe barrel 30 through the movement of the movable plug cover 40. Not only can the recovery rate of high-viscosity bone cement be effectively improved during the transfer process, but also the steps are simple, which can effectively reduce the time of the transfer process to achieve the effect of completing the preparation of the bone cement quickly and efficiently, and greatly increase the convenience of the preparation process of high-viscosity bone cement. Moreover, when collecting this high-viscosity bone cement, due to the friction between the bone cement and the container wall, the bone cement can be externally rotated during the forward-moving process and to achieve the effect of further eliminating air within it.

It should be further explained that in the bone cement mixing assembly 10 provided by the present invention, the first barrel open 242 and the second barrel open 32 can be connected in many different ways to make the stirring space 245 and the injection space 35 communicate with each other. The following lists several different connection structures as examples to illustrate.

Figure 7:
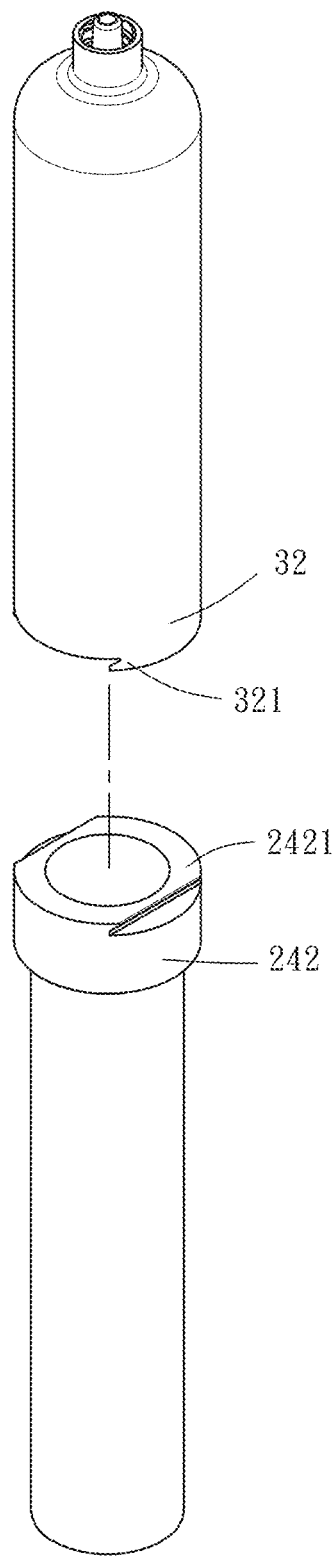
FIG. 7 is an exploded view of partial components of the bone cement mixing assembly provided by another embodiment of the present invention, which mainly shows the appearance structure of the mixer and the syringe barrel when the mixer and the syringe barrel are connected with a tenon.
Figure 8:
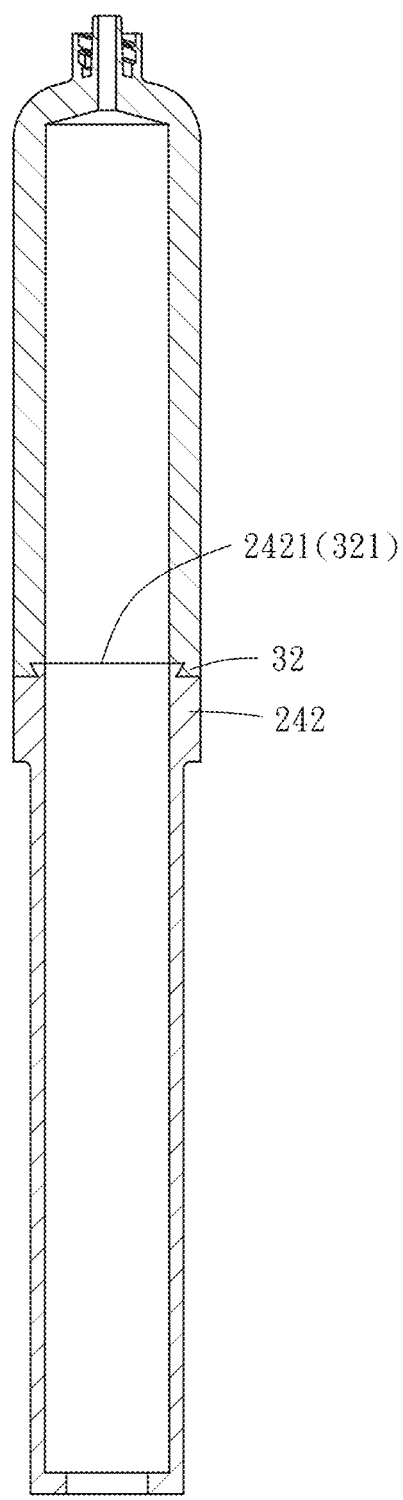
FIG. 8 is a cross-sectional view of FIG. 7 after combining.

As shown in FIGS. 7 and 8, in another embodiment of the present invention, the first barrel open 242 is a large-diameter section and has a tenon 2421, and the second barrel open 32 has a tenon groove 321, whereby the tenon 2421 can be interlocked with the tenon groove 321 to connect the first barrel open 242 and the second barrel open 32.

Figure 9:
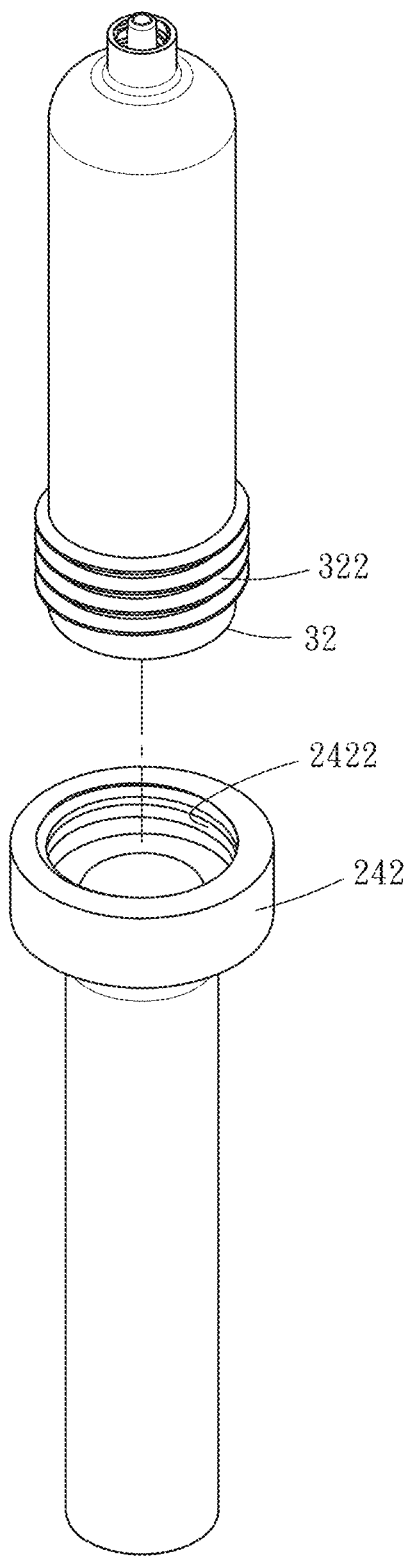
FIG. 9 is an exploded view of partial components of the bone cement mixing assembly provided by still another embodiment of the present invention, which mainly shows the appearance structure of the mixer and the syringe barrel when the mixer and the syringe barrel are connected in a mutually screw-locked manner.
Figure 10:
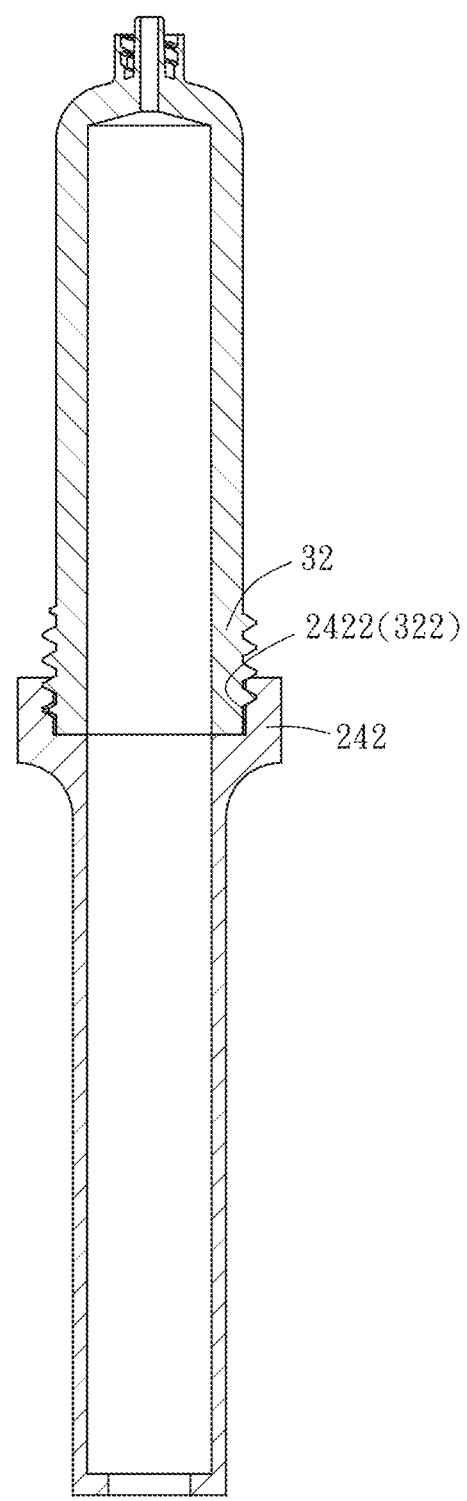
FIG. 10 is a cross-sectional view of FIG. 9 after combining.

As shown in FIGS. 9 and 10, in still another embodiment of the present invention, the first barrel open 242 is a large diameter section and has a female thread 2422, and the second barrel open 32 has a male thread 322. In this way, the female thread 2422 can be screwed with the male thread 322 to connect the first barrel open 242 and the second barrel open 32.

Figure 11:
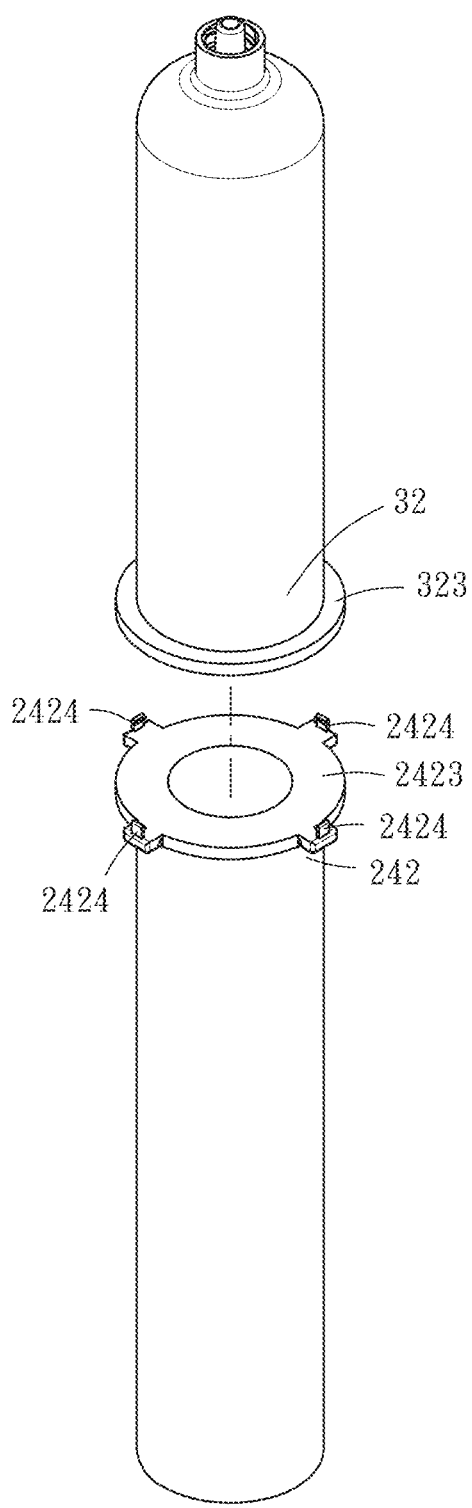
FIG. 11 is an exploded view of partial components of the bone cement mixing assembly provided by still another embodiment of the present invention, which mainly shows the appearance structure of the mixer and the syringe barrel when the mixer and the syringe barrel are connected in a snap-fit manner.
Figure 12:
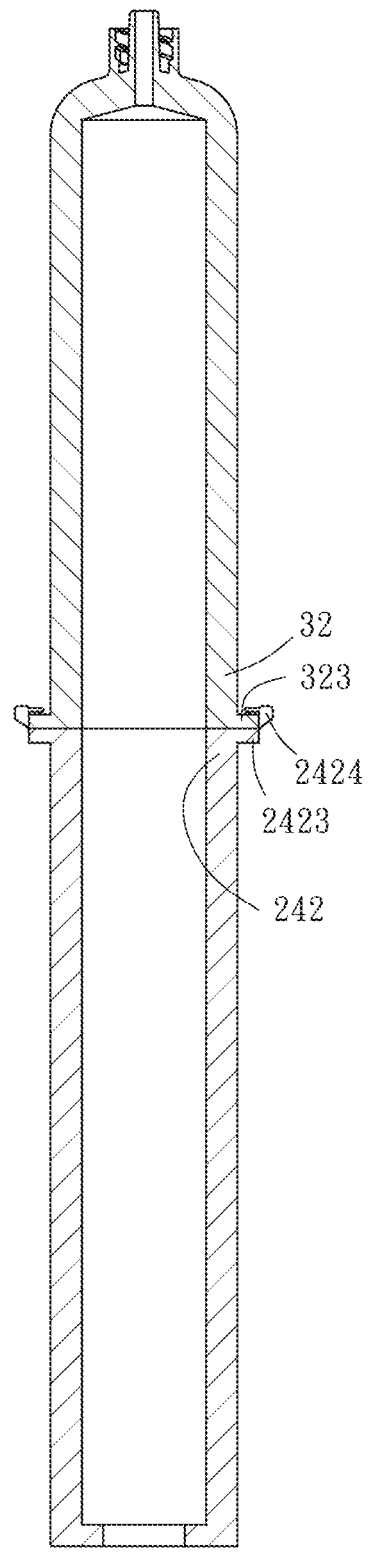
FIG. 12 is a cross-sectional view of FIG. 11 after combining.

As shown in FIGS. 11 and 12, in still another embodiment of the present invention, the first barrel open 242 has a first flange 2423 and at least two fasteners 2424. There are four fasteners 2424 in this embodiment, and these four fasteners 2424 are arranged at four relative positions on the periphery of the first flange 2423 at intervals. The second barrel open 32 has a second flange 323. The first flange 2423 abuts on the second flange 323 and then each fastener 2424 buckles the second flange 323 to connect the first barrel open 242 and the second barrel open 32.

Figure 13:
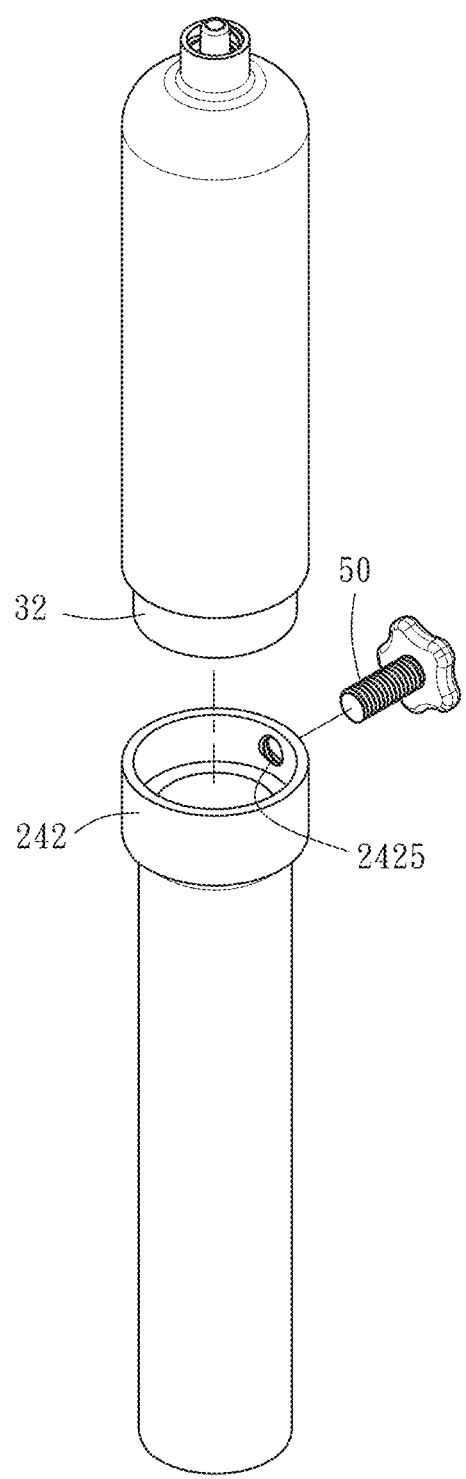
FIG. 13 is an exploded view of partial components of the bone cement mixing assembly provided by still another embodiment of the present invention, which mainly shows the appearance structure of the mixer and the syringe barrel when the mixer and the syringe barrel are connected with a lock screw.
Figure 14:
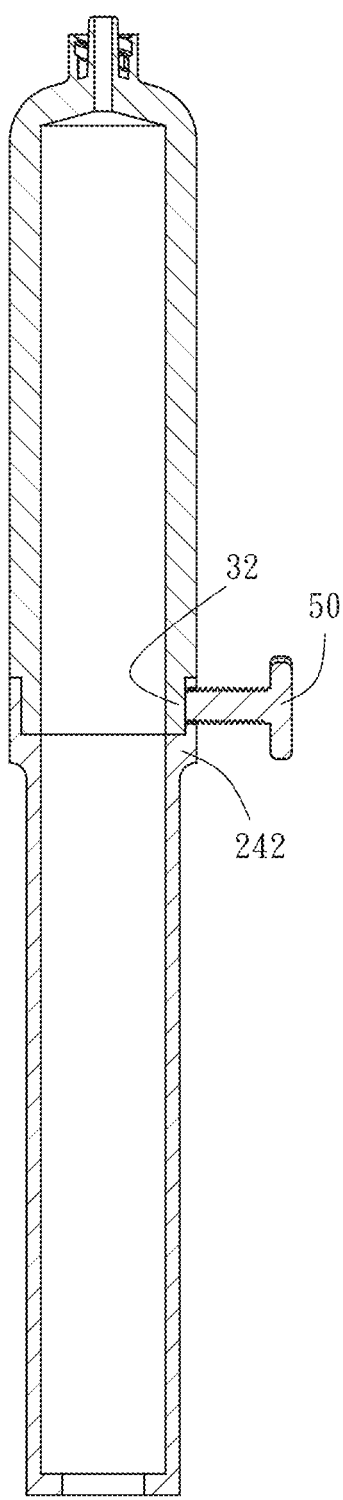
FIG. 14 is a cross-sectional view of FIG. 13 after combining.

As shown in FIGS. 13 and 14, in still another embodiment of the present invention, it further comprises a lock screw 50. The first barrel open 242 is a large diameter section and has a screw hole 2425. The second barrel open 32 is a small diameter section. The first barrel open 242 is sleeved on the second barrel open 32 and the lock screw 50 is passed through the screw hole 2425, so that the lock screw 50 is tightly propped against the second barrel open 32 to connect the first barrel open 242 and the second barrel open 32.

Figures 15, 16:
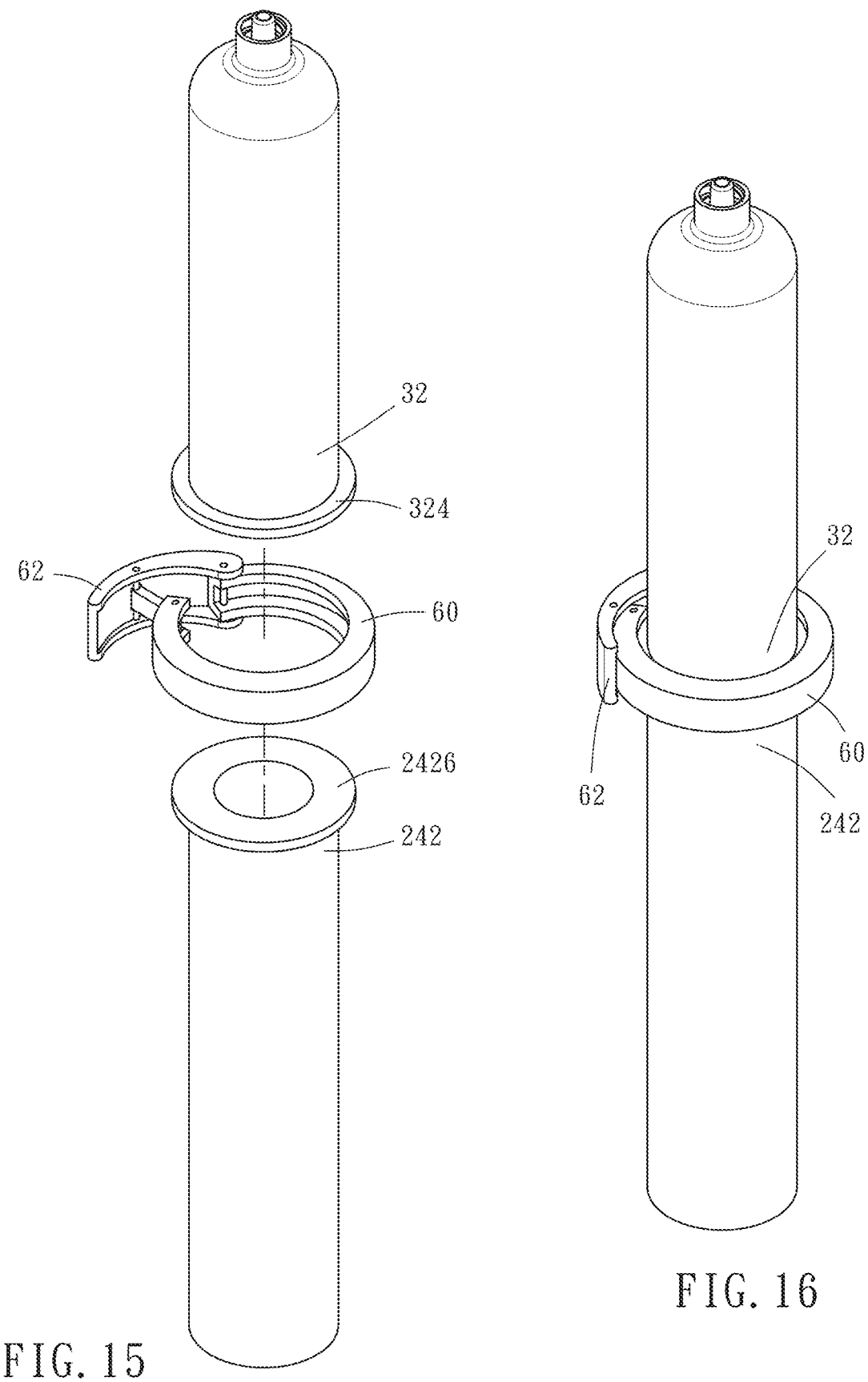
FIG. 15 is an exploded view of partial components of the bone cement mixing assembly provided by still another embodiment of the present invention, which mainly shows the appearance structure of the mixer and the syringe barrel when the mixer and the syringe barrel are connected with a quick buckle.
FIG. 16 is a cross-sectional view of FIG. 15 after combining.

As shown in FIGS. 15 and 16, in still another embodiment of the present invention, it further comprises a clamping ring 60 and a quick buckle 62. The first barrel open 242 has a first flange 2426, and the second barrel open 32 has a second flange 324. The clamping ring 60 is sleeved on the first flange 2426 and the second flange 324. When the quick buckle 62 is tightened, the radius of the clamping ring 60 becomes smaller, and the first flange 2426 and the second flange 324 are tightly connected, and then the first barrel open 242 and the second barrel open 32 are connected.

Figure 17:
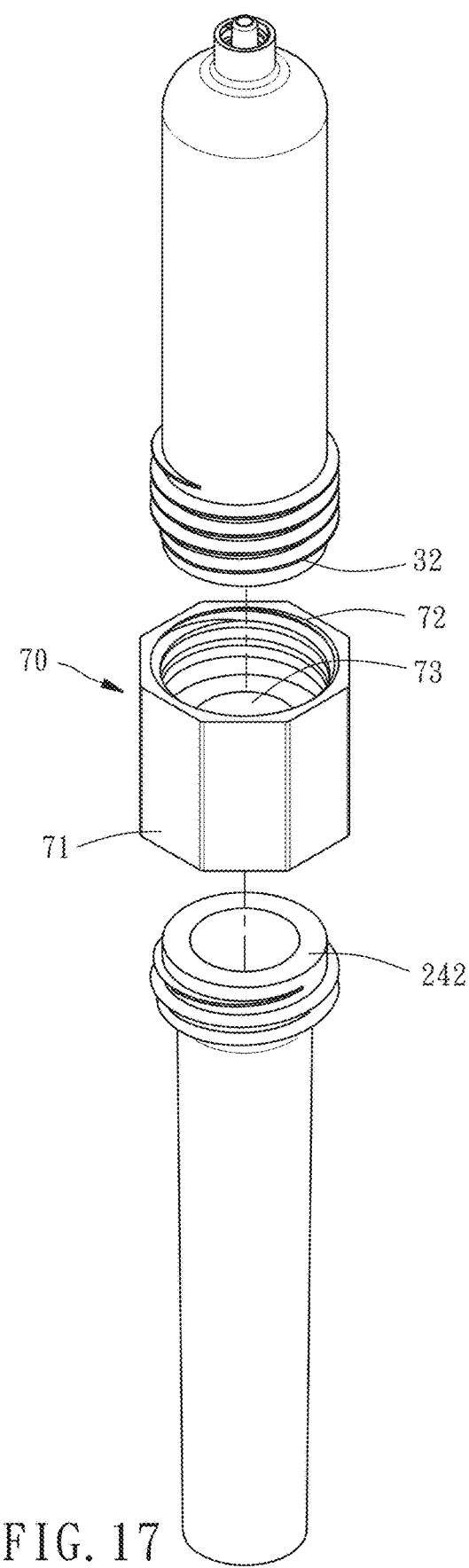
FIG. 17 is an exploded view of partial components of the bone cement mixing assembly provided by still another embodiment of the present invention, which mainly shows the appearance structure of the mixer and the syringe barrel when the mixer and the syringe barrel are connected with a connector.
Figure 18:
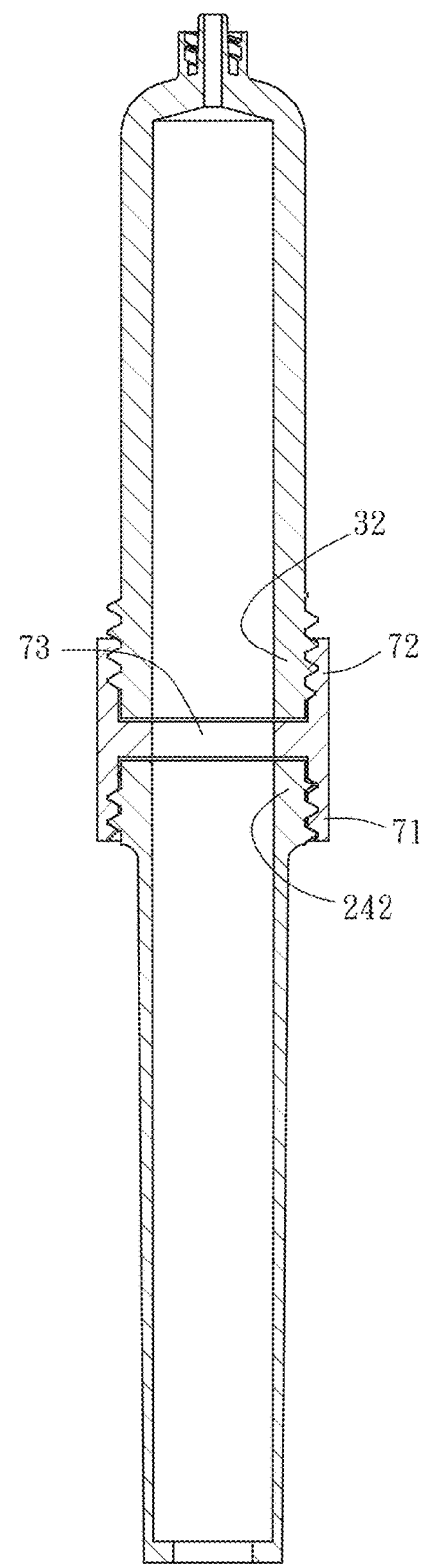
FIG. 18 is a cross-sectional view of FIG. 17 after combining.

As shown in FIGS. 17 and 18, in still another embodiment of the present invention, it further comprises a connector 70. This connector 70 has a first connecting portion 71, a second connecting portion 72 and a connecting channel 73. The first connecting portion 71 is detachably sleeved on the first barrel open 242. The second connecting portion 72 is detachably sleeved on the second barrel open 32. The connecting channel 73 connects the first connecting portion 71 and the second connecting portion 72. In this embodiment, the connector 70 is an octagonal three-dimensional structure. The first connecting portion 71 and the second connecting portion 72 are flanges respectively protruding from the middle part of the connector 70 to both sides along the longitudinal direction, and the inner side of each flange is provided with internal threads. The first connecting portion 71 and the second connecting portion 72 can be screwed to the first barrel open 242 and the second barrel open 32 respectively, and then the first barrel open 242 and the second barrel open 32 are connected, and the connecting channel 73 penetrates the middle part to connect the first connecting portion 71 with the second connecting portion 72. The inner diameter d1 of the stirring barrel 24 is equal to the inner diameter d2 of the syringe barrel 30 and the inner diameter d3 of the connecting channel 73, so that the stirring space 245, the connecting channel 73 and the injection space 35 together form a bone cement transfer channel for the movable plug cover 40 to move from the stirring barrel 24 to the syringe barrel 30.

It must be noted here that the above detailed description in conjunction with the drawings is only provided for the purpose of illustrating the technical content and features of the present invention. Anyone who has general knowledge in the field of the present invention, after understanding the technical content and features of the present invention, under the concept of the present invention, all simple modifications, replacements or reductions of components should all fall within the scope of the patent application disclosed in the present invention.

What is claimed is:

1. A bone cement mixing assembly, comprising:
a mixer, said mixer comprising a stirring rod and a stirring barrel, said stirring rod comprising a holding end, a rod body and a stirring end, said stirring barrel comprising a barrel cover, a first barrel open, a first barrel body, a first barrel bottom and a stirring space, said barrel cover being detachably sleeved on said first barrel open, said stirring end movably passing through said barrel cover, said stirring space being located in said first barrel body, said first barrel bottom comprising an opening;
a syringe barrel, said syringe barrel comprising a second barrel open, a second barrel body, a second barrel bottom and an injection space located in said second barrel body, said second barrel bottom comprising an injection port; and
a movable plug cover, said movable plug cover having an outer diameter slightly less than or equal to an inner diameter of said stirring barrel and an inner diameter of said syringe barrel, said movable plug cover being movably arranged in said stirring space or said injection space;
wherein said first barrel open is optionally sleeved by said barrel cover or connected to said second barrel open, when said barrel cover is sleeved on said first barrel open, said stirring end movably passes through said barrel cover and extends into said stirring space, when said first barrel open is connected to said second barrel open, said stirring space and said injection space are connected to each other.

2. The bone cement mixing assembly as claimed in claim 1, wherein said first barrel open comprises a tenon, said second barrel open comprises a tenon groove, and said tenon and said tenon groove are embedded in each other, thereby connecting said first barrel open and said second barrel open.

3. The bone cement mixing assembly as claimed in claim 1, wherein said first barrel open comprises a female thread, said second barrel open comprises a male thread, and said female thread and said male thread are screwed to each other to connect said first barrel open and said second barrel open.

4. The bone cement mixing assembly as claimed in claim 1, wherein said first barrel open comprises a first flange and at least two fasteners spaced apart on a periphery of said first flange, said second barrel open comprises a second flange abutted against said first flange and secured to said first flange by said fasteners to connect said first barrel open and said second barrel open.

5. The bone cement mixing assembly as claimed in claim 1, further comprising a lock screw, wherein said first barrel open comprises a screw hole, said first barrel open is sleeved on said second barrel open, said lock screw is threaded into said screw hole and propped against said second barrel open.

6. The bone cement mixing assembly as claimed in claim 1, further comprising a clamping ring and a quick buckle, wherein said first barrel open further comprises a first flange, said second barrel open further comprises a second flange, said clamping ring is sleeved on said first flange and said second flange, when said quick buckle is tightened, a radius of said clamping ring is reduced to tightly fasten said first flange and said second flange.

7. The bone cement mixing assembly as claimed in claim 1, further comprising a connector, said connector comprising a first connecting portion, a second connecting portion and a connecting channel, said first connecting portion being detachably sleeved on said first barrel open, said second connecting portion being detachably sleeved on said second barrel open, said connecting channel connecting said first connecting portion and said second connecting portion, said first barrel open being optionally sleeved by said first connecting portion, wherein when said first connecting portion is sleeved on said first barrel open and said second connecting portion is sleeved on said second barrel open, said second barrel open is connected to said first barrel open, and said stirring space and said injection space are connected to each other.

8. The bone cement mixing assembly as claimed in claim 7, wherein the inner diameter of said stirring barrel is equal to the inner diameter of said syringe barrel and an inner diameter of said connecting channel.

9. The bone cement mixing assembly as claimed in claim 1, wherein said holding end comprises a grip.

10. The bone cement mixing assembly as claimed in claim 1, wherein said first barrel body is made of a transparent material.

11. The bone cement mixing assembly as claimed in claim 1, wherein said barrel cover comprises a through hole, and said rod body is movably arranged in said through hole of said barrel cover.

12. The bone cement mixing assembly as claimed in claim 1, wherein said stirring end comprises a stirring ring and four connecting ribs, each said connecting rib having one end thereof connected to said rod body and an opposite end thereof connected to said stirring ring.

* * * * *